(12) United States Patent
Pasquier et al.

(10) Patent No.: US 7,393,366 B2
(45) Date of Patent: Jul. 1, 2008

(54) AGENTS FOR COLORING KERATIN FIBERS

(75) Inventors: Cécile Pasquier, Marly (CH); Eric Tinguely, Fribourg (CH); Otto Göttel, Marly (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 194 days.

(21) Appl. No.: 11/341,050

(22) Filed: Jan. 27, 2006

(65) Prior Publication Data

US 2007/0011821 A1    Jan. 18, 2007

(30) Foreign Application Priority Data

Jan. 27, 2005    (DE)    ............... 10 2005 003 821

(51) Int. Cl.
*A61Q 5/10*    (2006.01)
*C07D 277/08*    (2006.01)

(52) U.S. Cl. ............... 8/405; 8/406; 8/408; 8/437; 8/461; 8/465; 8/570; 8/571; 8/572; 8/574; 8/575; 8/576; 548/146; 548/215; 548/300.1

(58) Field of Classification Search ............... 8/405, 8/406, 407, 408, 437, 461, 465, 570, 571, 8/572, 574, 575, 576; 548/146, 215, 300, 548/300.1

See application file for complete search history.

(56) References Cited

U.S. PATENT DOCUMENTS 5,980,587 A * 11/1999 Samain ............... 8/426

FOREIGN PATENT DOCUMENTS

| DE | 19618595 A1 | 11/1997 |
| DE | 20011207 U1 | 10/2001 |
| EP | 0648813 A1 | 4/1995 |
| WO | WO-95/01722 A1 | 1/1995 |
| WO | WO-97/20545 A1 | 6/1997 |
| WO | WO-01/10379 A2 | 2/2001 |
| WO | WO-03/030847 A1 | 4/2003 |

OTHER PUBLICATIONS

STIC Search Report dated Nov. 1, 2007.*
International Search Report, Application No. PCT/US2006/002495, dated Jun. 7, 2006 (5 pages).

* cited by examiner

*Primary Examiner*—Eisa B Elhilo
(74) *Attorney, Agent, or Firm*—Idris N. McKelvey

(57) ABSTRACT

The present invention relates to agents for coloring keratin fibers which comprise at least one zwitterionic azo dye of the general formula (I)

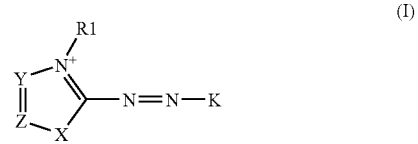

where R1 is an alkylsulfonate radical of the formula (II),

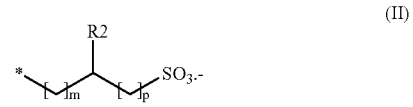

14 Claims, No Drawings

AGENTS FOR COLORING KERATIN FIBERS

FIELD OF THE INVENTION

The present invention relates to agents for coloring keratin fibers, such as, for example, wool, furs and, in particular, human hair, comprising zwitterionic azo dyes.

BACKGROUND OF THE INVENTION

For the color-changing treatment of keratin fibers use is usually made of two coloring methods. In the first method, the coloration is produced with so-called oxidative or permanent colorants using a mixture of various developer substances and coupler substances and an oxidizing agent. If required, in this method, so-called direct (nonoxidative) dyes can be added to round off the coloring result or to produce particular color effects. The second method uses exclusively direct dyes, which are applied to the fibers in a suitable carrier mass. This method is easy to use, exceptionally gentle and is characterized by low damage to keratin fibers. The direct dyes used here are subject to a large number of requirements. For example, they have to be acceptable from a toxicological and dermatological point of view and allow the attainment of colorations in the desired intensity, which, inter alia, also requires adequate solubility in water. In addition, good light-fastness, acid fastness and rubbing fastness is required for the colorations achieved.

Compared with oxidative colorations, nonoxidative colorations, however, generally have lower durability and a poorer evening out of color. In addition, direct colorants are generally not able to "lighten" the hair since many direct dyes do not withstand the oxidizing agents required for the lightening and/or the required pH of greater than or equal to 9.

WO 95/01722 and WO 97/20545 disclose colorants which comprise cationic azo dyes.

DETAILED DESCRIPTION OF THE INVENTION

Surprisingly, it has now been found that certain zwitterionic azo dyes intensely color keratin fibers, and are oxidation-stable, and thus can also be used in oxidative coloring systems.

The present invention therefore provides
(a) an agent for the nonoxidative coloring of keratin fibers, in particular human hair;
(b) an agent for the simultaneous lightening and coloring of keratin fibers, in particular human hair, which, besides the dye of the formula (I), comprises an oxidizing agent; and
(c) an oxidative colorant for keratin fibers, in particular human hair, based on at least one oxidation dye precursor; where the agents (a), (b) and (c) are notable for the fact that they each comprise at least one zwitterionic azo dye of the general formula (I);

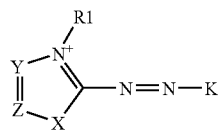
(I)

in which
R1 is an alkyl sulfonate radical of the formula (II);

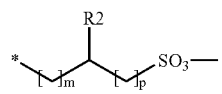
(II)

R2 is hydrogen or a hydroxyl group;
m is 0 to (n−1);
p is 0 to (n−1) where m+p=(n−1);
n is an integer from 1 to 6;
X is oxygen, sulfur, N—R3 or C—R4;
Y is C—R5, nitrogen, N—R6, sulfur or oxygen;
Z is C—R7 or nitrogen;
with the proviso that the heterocycle of the formula (I) comprises at least two and at most three heteroatoms, where the heterocycle has at most one sulfur atom or oxygen atom;
R3 and R6 may be identical or different and, independently of one another, are a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group or a substituted or unsubstituted benzyl group;
R4, R5 and R7 may be identical or different and, independently of one another, are hydrogen, a halogen atom (F, Cl, Br, I), a saturated or unsaturated ($C_1$-$C_{12}$)-alkyl group, a ($C_1$-$C_{12}$)-alkyl group substituted by a halogen atom (F, Cl, Br, I), a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group or a naphthyl group, or a substituted or unsubstituted heteroaryl group; or if Y and Z are C—R5 and C—R7, the radical groups R5 and R7, together with the remaining molecule, can form a heterocyclic or carbocyclic, saturated or unsaturated, substituted or unsubstituted ring system;
or if X and Y are C—R4 and C—R5, the radical groups R4 and R5, together with the remaining molecule, can form a heterocyclic or carbocyclic, saturated or unsaturated, substituted or unsubstituted ring system;
K is a radical group of the aniline or phenol series or a heterocyclic radical group.

Among the abovementioned compounds of the formula (I), preference is given to those in which n is 2 or 3, and R2 is hydrogen. Particular preference is given to compounds of the formula (I) in which n is 2 or 3, R2 is hydrogen, and K is a radical group of the formula K1,

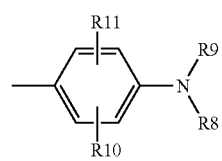
K1 in which R8 and R9 may be identical or different and, independently of one another, are a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-$(C_1-C_{12})$-alkyl group, a substituted or unsubstituted phenyl group or a benzyl group, or R8 and R9, together with the nitrogen atom, form a 5-membered to 6-membered ring system, which may comprise a further heteroatom;

R10 and R11 may be identical or different and, independently of one another, are hydrogen, a halogen atom (F, Cl, Br, I), a saturated or unsaturated $(C_1-C_{12})$-alkyl group, a $(C_1-C_{12})$-alkyl group substituted by a halogen atom (F, Cl, Br, I), a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted or unsubstituted C(O)O-phenyl group.

Examples of suitable compounds of the general formula (I) which may be mentioned are: 4-(2-{[4-(dimethylamino)phenyl]diazenyl)}-1,3-thiazol-3-ium-3-yl)-1-butanesulfonate, 3-(2-{[4-(dimethylamino)phenyl]diazenyl}-1,3-thiazol-3-ium-3-yl)-1-propanesulfonate, 4-(2-{[4-(dimethylamino)phenyl]diazenyl)}-4-methyl-1,3-thiazol-3-ium-3-yl)-1-butanesulfonate, 3-(2-{[4-(dimethyl-amino)phenyl]diazenyl}-4-methyl-1,3-thiazol-3-ium-3-yl)-1-propane-sulfonate, 4-(2-{[4-(dimethylamino)phenyl]diazenyl}-5-methyl-1,3-thiazol-3-ium-3-yl)-1-butanesulfonate, 3-(2-{[4-(dimethylamino)phenyl]diazenyl}-5-methyl-1,3-thiazol-3-ium-3-yl)-1-propanesulfonate, 4-(2-{[4-(dimethyl-amino)phenyl]diazenyl}-4,5-dimethyl-1,3-thiazol-3-ium-3-yl)-1-butanesulfonate, 3-(2-{[4-(dimethylamino)phenyl]diazenyl}-4,5-dimethyl-1,3-thiazol-3-ium-3-yl)-1-propanesulfonate, 4-(5-bromo-2-{[4-(dimethyl-amino)phenyl]diazenyl}-1,3-thiazol-3-ium-3-yl)-1-butanesulfonate, 3-(5-bromo-2-{[4-(dimethylamino)phenyl]diazenyl}-1,3-thiazol-3-ium-3-yl)-1-propanesulfonate, 4-(2-{[4-(dimethylamino)phenyl]diazenyl}-5-methoxy-1,3-thiazol-3-ium-3-yl)-1-butanesulfonate, 3-(2-{[4-(dimethylamino)-phenyl]diazenyl}-5-methoxy-1,3-thiazol-3-ium-3-yl)-1-propanesulfonate, 4-(2-{[4-(dimethylamino)phenyl]diazenyl}-5-nitro-1,3-thiazol-3-ium-3-yl)-1-butanesulfonate, 3-(2-{[4-(dimethylamino)phenyl]diazenyl}-5-nitro-1,3-thiazol-3-ium-3-yl)-1-propanesulfonate, 4-[(2-{4-[benzyl(methyl)amino]phenyl}diazenyl)-1,3-thiazol-3-ium-3-yl]-1-butanesulfonate, 3-[(2-{4-[benzyl(methyl)amino]phenyl}diazenyl)-1,3-thiazol-3-ium-3-yl]-1-propanesulfonate, 4-(2-{[4-(1-pyrrolidinyl)phenyl]diazenyl}-1,3-thiazol-3-ium-3-yl)-1-butanesulfonate, 3-(2-{[4-(1-pyrrolidinyl)phenyl]diazenyl}-1,3-thiazol-3-ium-3-yl)-1-propanesulfonate, 4-(2-{[4-(4-morpholinyl)phenyl]-diazenyl}-1,3-thiazol-3-ium-3-yl)-1-butanesulfonate, 3-(2-{4-(4-morpholinyl)phenyl]diazenyl}-1,3-thiazol-3-ium-3-yl)-1-propanesulfonate, 4-(2-{[4-(4-methyl-1-piperazinyl)phenyl]diazenyl}-1,3-thiazol-3-ium-3-yl)-1-butanesulfonate, 3-(2-{[4-(4-methyl-1-piperazinyl)phenyl]diazenyl}-1,3-thiazol-3-ium-3-yl)-1-propanesulfonate, 4-(2-{[4-(dimethylamino)phenyl]-diazenyl}-1,3-benzothiazol-3-ium-3-yl)-1-butanesulfonate, 3-(2-{[4-(dimethylamino)phenyl]diazenyl}-1,3-benzothiazol-3-ium-3-yl)-1-propanesulfonate, 4-(2-{[4-(dimethylamino)phenyl]diazenyl}-6-methoxy-1,3-benzothiazol-3-ium-3-yl)-1-butanesulfonate, 3-(2-{[4-(dimethylamino)-phenyl]diazenyl}-6-methoxy-1,3-benzothiazol-3-ium-3-yl)-1-propane-sulfonate, 4-[2-({4-[benzyl(ethyl)amino]phenyl}diazenyl)-1,3-thiazol-3-ium-3-yl]-1-butanesulfonate, 3-[2-({4-[benzyl(ethyl)amino]phenyl}diazenyl)-1,3-thiazol-3-ium-3-yl]-1-propanesulfonate, 4-[2-({4-[benzyl(ethyl)amino]phenyl}diazenyl)-4-methyl-1,3-thiazol-3-ium-3-yl]-1-butanesulfonate, 3-[2-({4-[benzyl(ethyl)amino]phenyl}diazenyl)-4-methyl-1,3-thiazol-3-ium-3-yl]-1-propanesulfonate, 4-[2-({4-[benzyl(ethyl)amino]phenyl}diazenyl)-5-methyl-1,3-thiazol-3-ium-3-yl]-1-butanesulfonate, 3-[2-({4-[benzyl(ethyl)-amino]phenyl}diazenyl)-5-methyl-1,3-thiazol-3-ium-3-yl]-1-propane-sulfonate, 4-[2-({4-[benzyl(ethyl)amino]phenyl}diazenyl)-4,5-dimethyl-1,3-thiazol-3-ium-3-yl]-1-butanesulfonate, 3-[2-({4-[benzyl(ethyl)amino]-phenyl}diazenyl)-4,5-dimethyl-1,3-thiazol-3-ium-3-yl]-1-propanesulfonate, 4-[2-({4-[benzyl(ethyl)amino]-2-methylphenyl}diazenyl)-1,3-thiazol-3-ium-3-yl]-1-butanesulfonate, 3-[2-({4-[benzyl(ethyl)amino]-2-methylphenyl}diazenyl)-1,3-thiazol-3-ium-3-yl]-1-propanesulfonate, 4-[2-({4-[benzyl(ethyl)amino]-2-methylphenyl}diazenyl)-4-methyl-1,3-thiazol-3-ium-3-yl]-1-butanesulfonate, 3-[2-({4-[benzyl(ethyl)amino]-2-methylphenyl}diazenyl)-4-methyl-1,3-thiazol-3-ium-3-yl]-1-propane-sulfonate, 4-[2-({4-[benzyl(ethyl)amino]-2-methylphenyl}diazenyl)-5-methyl-1,3-thiazol-3-ium-3-yl]-1-butanesulfonate, 3-[2-({4-[benzyl(ethyl)-amino]-2-methylphenyl}diazenyl)-5-methyl-1,3-thiazol-3-ium-3-yl]-1-propanesulfonate, 4-[2-({4-[benzyl(ethyl)amino]-2-methylphenyl}diazenyl)-4,5-dimethyl-1,3-thiazol-3-ium-3-yl]-1-butanesulfonate, 3-[2-({4-[benzyl-(ethyl)amino]-2-methylphenyl}diazenyl)-4,5-dimethyl-1,3-thiazol-3-ium-3-yl]-1-propanesulfonate, 4-(2-{[4-(dimethylamino)phenyl]diazenyl}-1-methyl-1H-imidazol-3-ium-3-yl)-1-butanesulfonate, 3-(2-{[4-(dimethyl-amino)phenyl]diazenyl}-1-methyl-1H-imidazol-3-ium-3-yl)-1-propane-sulfonate, 4-{2-[(4-aminophenyl)diazenyl]-1-methyl-1H-imidazol-3-ium-3-yl}-1-butanesulfonate, 3-{2-[(4-aminophenyl)diazenyl]-1-methyl-1H-imidazol-3-ium-3-yl}-1-propanesulfonate, 4-(1-methyl-2-{[4-(methylamino)phenyl]diazenyl}-1H-imidazol-3-ium-3-yl)-1-butanesulfonate, 3-(1-methyl-2-{[4-(methylamino)phenyl]diazenyl}-1H-imidazol-3-ium-3-yl)-1-propanesulfonate, 4-(2-{[4-(dimethylamino)phenyl]-diazenyl}-1,4,5-trimethyl-1H-imidazol-3-ium-3-yl)-1-butanesulfonate, 3-(2-{[4-(dimethylamino)phenyl]diazenyl}-1,4,5-trimethyl-1H-imidazol-3-ium-3-yl)-1-propanesulfonate, 4-(5-{[4-(dimethylamino)phenyl]diazenyl}-4-methyl-4H-1,2,4-triazol-1-ium-1-yl)-1-butanesulfonate, 3-(5-{[4-(dimethylamino)phenyl]diazenyl}-4-methyl-4H-1,2,4-triazol-1-ium-1-yl)-1-propanesulfonate, 4-(2-{[4-(dimethylamino)phenyl]diazenyl}-1,3,4-thiadiazol-3-ium-3-yl)-1-butanesulfonate, 3-(2-{[4-(dimethylamino)-phenyl]diazenyl}-1,3,4-thiadiazol-3-ium-3-yl)-1-propanesulfonate, 4-(5-{[4-(dimethylamino)phenyl]diazenyl}-1,2,4-thiadiazol-4-ium-4-yl)-1-butane-sulfonate, 3-(5-{[4-(dimethylamino)phenyl]diazenyl}-1,2,4-thiadiazol-4-ium-4-yl)-1-propanesulfonate, 3-(3-{[4-(dimethylamino)phenyl]diazenyl}-1-methyl-1H-pyrazol-2-ium-2-yl)-1-propanesulfonate, 4-(3-{[4-(dimethylamino)phenyl]diazenyl}-1-methyl-1H-pyrazol-2-ium-2-yl)-1-butanesulfonate, 3-(3-{[4-(dimethylamino)phenyl]diazenyl}isoxazol-2-ium-2-yl)-1-propanesulfonate, 4-(3-{[4-(dimethylamino)phenyl]diazenyl}-isoxazol-2-ium-2-yl)-1-butanesulfonate, 4-{2-[(1-methyl-2-phenyl-1H-indol-3-yl)diazenyl]-1,3-thiazol-3-ium-3-yl}-1-butanesulfonate, 3-{2-[(1-methyl-2-phenyl-1H-indol-3-yl)diazenyl]-1,3-thiazol-3-ium-3-yl}-1-propanesulfonate, 4-{2-(1,2-dimethyl-1H-indol-3-yl)diazenyl]-1,3-thiazol-3-ium-3-yl}-1-butane-sulfonate and 3-{2-(1,2-dimethyl-1H-indol-3-yl)diazenyl]-1,3-thiazol-3-ium-3-yl}-1-propanesulfonate.

The dyes of the formula (I) are present in the colorant according to the invention preferably in an amount of from 0.01 to 10% by weight, in particular 0.1 to 8% by weight.

To extend the color pallet, the colorant according to the invention can (a) besides the dyes of the formula (I), additionally also comprise further known direct synthetic dyes from the group consisting of nitro dyes, azo dyes, anthraquinone dyes, triphenylmethane dyes and basic or acidic dyes, and natural direct dyes, alone or in a mixture with one another, for example 1,4-bis[(2-hydroxyethyl)amino]-2-nitrobenzene, 1-(2-hydroxyethyl)amino-2-nitro-4-[di(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene, (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylaminobenzoic acid (HC Blue No. 13), 1-(2-aminoethylamino)-4-[di(2-hydroxyethyl)amino]-2-nitrobenzene, 4-(di(2-hydroxyethyl)amino)-2-nitro-1-phenylaminobenzene, 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-((2-hydroxyethyl)methylamino)-1-(methylamino)-2-nitrobenzene, 1-amino-4-((2,3-dihydroxypropyl)amino)-5-methyl-2-nitrobenzene, 1-amino-4-(methylamino)-2-nitrobenzene, 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-((2-hydroxyethyl)amino)-2-nitropyridine, 3-amino-6-((2-hydroxyethyl)amino)-2-nitropyridine, 3-amino-6-(ethylamino)-2-nitropyridine, 3-((2-hydroxyethyl)amino)-6-(methylamino)-2-nitropyridine, 3-amino-6-(methylamino)-2-nitropyridine, 6-(ethylamino)-3-((2-hydroxyethyl)amino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-(di(2-hydroxyethyl)amino)-5-nitrophenol, 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methyl amino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride, (HC Yellow No.9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis[(2-hydroxyethyl)amino]-5-nitrobenzene (HC Yellow No. 10), 1-amino-4-((2-aminoethyl)amino)-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene, (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-((2-hydroxyethyl)amino)-4-methyl-1-nitrobenzene, 4-chloro-3-((2-hydroxyethyl)amino)-1-nitrobenzene, 2,4-dinitro-1-hydroxynaphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 1,4-diamino-9,10-anthraquinone (CI61 100, Disperse Violet No. 1), 1-amino-4-(methylamino)-9,10-anthraquinone (CI61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-(6-((3-chloro-4-(methylamino)phenyl)imino)-4-methyl-3-oxo-1,4-cyclohexadien-1-yl)urea (HC Red No. 9), 2-((4-(di(2-hydroxyethyl)amino)phenyl)amino)-5-((2-hydroxyethyl)amino)-2,5-cyclohexadiene-1,4-dione (HC Green No. 1), 5-hydroxy-1,4-naphthoquinone (CI75500, Natural Brown No. 7), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis(dicyanomethylene)indane, 9-(dimethylamino)benzo[a]phenoxazin-7-ium chloride (CI51175; Basic Blue No. 6), di[4-(diethylamino)phenyl][4-(ethylamino)naphthyl]carbenium chloride (CI42595; Basic Blue No. 7), di(4-(dimethylamino)phenyl)(4-(methylphenylamino)naphthalen-1-yl)carbenium chloride (CI42563; Basic Blue No. 8), 3,7-di(dimethylamino)phenothiazin-5-ium chloride (CI52015; Basic Blue No. 9), di[4-(dimethylamino)phenyl][4-(phenylamino)naphthyl]carbenium chloride (CI44045; Basic Blue No. 26), 2-[(4-(ethyl(2-hydroxyethyl)amino)-phenyl)azo]-6-methoxy-3-methylbenzothiazolium methylsulfate (Cl11154; Basic Blue No. 41), Basic Blue No. 77, 8-amino-2-bromo-5-hydroxy-4-imino-6-[(3-(trimethylammonio)phenyl)amino]-1 (4H)-naphthalenone chloride (CI56059; Basic Blue No. 99), bis[4-(dimethylamino)phenyl][4-(methylamino)phenyl]carbenium chloride (CI42535; Basic Violet No. 1), tri(4-amino-3-methylphenyl)carbenium chloride (CI42520; Basic Violet No. 2), tris[4-(dimethylamino)phenyl]carbenium chloride (CI42555; Basic Violet No. 3), 2-[3,6-(diethylamino)dibenzopyranium-9-yl]benzoyl chloride (CI45170;

Basic Violet No. 10), di(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzenaminium chloride (CI12605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)-azo-1H-imidazol-3-ium chloride (Basic Red No. 51), 2-hydroxy-1-[(2-methoxyphenyl)azo]-7-(trimethylammonio)naphthalene chloride (CI12245; Basic Red No. 76), 2-[2-((2,4-dimethoxyphenyl)amino)ethenyl]-1,3,3-trimethyl-3H-indol-1-ium chloride (CI48055; Basic Yellow No. 11), 3-methyl-1-phenyl-4-[(3-(trimethylammonio)phenyl)azo]pyrazol-5-one chloride (CI12719; Basic Yellow No. 57), di[4-(dimethylamino)phenyl]-iminomethane hydrochloride (CI41000; Basic Yellow No. 2), 1-methyl-4-((methylphenylhydrazono)methyl)pyridinium methylsulfate (Basic Yellow No. 87), bis[4-(diethylamino)phenyl]phenylcarbenium hydrogensulfate (1:1) (CI42040; Basic Green No. 1), di(4-(dimethylamino)phenyl)-phenyl-methanol (CI42000; Basic Green No. 4), 1-(2-morpholinium-propylamino)-4-hydroxy-9,10-anthraquinone methylsulfate, 1-[(3-(dimethylpropylaminium)propyl)amino]-4-(methylamino)-9,10-anthraquinone chloride, 1-[di(2-hydroxyethyl)amino]-3-methyl-4-[(4-nitrophenyl)azo] benzene (CI11210, Disperse Red No. 17), 1-[di(2-hydroxyethyl)amino]-4-[(4-nitrophenyl)azo]benzene (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]pyridine, 2-((4-(acetylamino)phenyl)azo)-4-methylphenol (CI11855; Disperse Yellow No. 3), 2-((4-(ethyl(2-hydroxyethyl)amino)-2-methylphenyl)azo)-5-nitro-1,3-thiazole (CI111935; Disperse Blue No. 106), 6-hydroxy-5-[(4-sulfophenyl)azo]-2-naphthalenecarboxylic acid disodium salt (CI15985; Food Yellow No. 3; FD&C Yellow No. 6), 2,4-dinitro-1-naphthol-7-sulfonic acid disodium salt (CI10316; Acid Yellow No. 1; Food Yellow No. 1), 2-(indane-1,3-dion-2-yl)quinoline-x,x-sulfonic acid (mixture of mono- and disulfonic acid) (CI47005; D&C Yellow No. 10; Food Yellow No. 13, Acid Yellow No. 3), 5-hydroxy-1-(4-sulfophenyl)-4-[(4-sulfophenyl)azo]pyrazole-3-carboxylic acid trisodium salt (CI19140; Food Yellow No. 4; Acid Yellow No. 23), 9-(2-carboxyphenyl)-6-hydroxy-3H-xanthen-3-one (CI45350; Acid Yellow No. 73; D&C Yellow No. 8), 4-((4-amino-3-sulfophenyl)azo)benzenesulfonic acid disodium salt (CI13015, Acid Yellow No. 9), 5-[(2,4-dinitrophenyl)amino]-2-phenylaminobenzenesulfonic acid sodium salt (CI10385; Acid Orange No. 3), 4-[(2,4-dihydroxyphenyl)azo]benzenesulfonic acid monosodium salt (CI14270; Acid Orange No. 6), 4-[(2-hydroxynaphth-1-yl)azo]benzenesulfonic acid sodium salt (CI15510; Acid Orange No. 7), 4-((2-hydroxynaphthalen-1-yl)azo)-3-methylbenzenesulfonic acid sodium salt (CI15575; Acid Orange No. 8), 4-[(2,4-dihydroxy-3-[(2,4-dimethylphenyl)azo]phenyl)azo]benzenesulfonic acid sodium salt (CI20170; Acid Orange No. 24), 3',6'-dihydroxy-4',5'-diiodospiro(isobenzofuran-1(3H)-9'-(9H)xanthen)-3-one (CI45425, D&C Orange No. 10), 4-hydroxy-3-[(4-sulfonaphth-1-yl)azo]-1-naphthalenesulfonic acid disodium salt (CI14720; Acid Red No. 14), 4-hydroxy-3-[(2-methoxyphenyl)azo]-1-naphthalenesulfonic acid monosodium salt (CI14710; Acid Red No. 4), 6-hydroxy-5-[(4-sulfonaphth-1-yl)azo]-2,4-naphthalenedisulfonic acid trisodium salt (CI16255; Ponceau 4R; Acid Red No. 18), 3-hydroxy-4-[(4-sulfonaphth-1-yl)azo]-2,7-naphthalenedisulfonic acid trisodium salt (CI16185; Acid Red No. 27), 8-amino-1-hydroxy-2-(phenylazo)-3,6-naphthalenedisulfonic acid disodium salt (CI17200; Acid Red No. 33), 5-(acetylamino)-4-hydroxy-3-[(2-methylphenyl)azo]-2,7-naphthalenedisulfonic acid disodium salt (CI1 8065; Acid Red No. 35), 2-(3-hydroxy-2,4,5,7-tetraiododibenzopyran-6-on-9-yl)benzoic acid disodium salt (CI45430; Acid Red No. 51), N-[6-(diethylamino)-9-(2,4-disulfophenyl)-3H-xanthen-3-ylidene]-N-ethylethaneammonium hydroxide, internal salt, sodium salt (CI45 100; Acid Red No. 52), 8-[(4-(phenylazo)phenyl)azo]-7-naphthol-1,3-disulfonic acid disodium salt (CI27290; Acid Red No. 73), 2',4',5',7'-tetrabromo-3',6'-dihydroxyspiro[isobenzofuran-1(3H),9'-[9H] xanthen]-3-one disodium salt (CI45380; Acid Red No. 87), 2',4',5',7'-tetrabromo-4,5,6,7-tetrachloro-3',6'-dihydroxyspiro[isobenzofuran-1(3H),9'-[9H]xanthen]-3-one disodium salt (CI45410; Acid Red No. 92), 3',6'-dihydroxy-4',5'-diiodospiro[isobenzofuran-1(3H),9'-(9H)-xanthen]-3-one disodium salt (CI45425; Acid Red No. 95), 2-hydroxy-3-((2-hydroxynaphth-1-yl)azo)-5-nitrobenzenesulfonic acid monosodium salt (CI1 5685; Acid Red No. 184), (2-sulfophenyl)di[4-(ethyl((4-sulfophenyl)methyl)amino)phenyl]carbenium disodium salt, betaine (CI42090; Acid Blue No. 9; FD&C Blue No. 1), 3-hydroxy-4-((4-methyl-2-sulfophenyl)azo)-2-naphthalenecarboxylic acid disodium salt (Cl15850; D&C Red No. 6), 6-hydroxy-5-((2-methoxy-5-methyl-4-sulfophenyl)azo)-2-naphthalenesulfonic acid disodium salt (CI16035; FD&C Red 40), 1,4-bis[(2-sulfo-4-methylphenyl)amino]-9,10-anthraquinone disodium salt (CI61570; Acid Green No. 25), bis[4-(dimethylamino)phenyl](3,7-disulfo-2-hydroxynaphth-1-yl)carbenium internal salt, monosodium salt (CI44090; Food Green No. 4; Acid Green No. 50), bis[4-(diethylamino)phenyl](2,4-disulfophenyl)carbenium internal salt, sodium salt (2:1) (CI42045; Food Blue No. 3; Acid Blue No. 1), bis[4-(diethylamino)phenyl](5-hydroxy-2,4-disulfophenyl)carbenium internal salt, calcium salt (2:1) (CI4205 1; Acid Blue No. 3), 1-amino-4-(cyclohexylamino)-9,10-anthraquinone-2-sulfonic acid sodium salt (CI62045; Acid Blue No. 62), 3,3-bis(3,5-dibromo-4-hydroxyphenyl)-4,5,6,7-tetrabromo-2,1(3h)-benzoxathiole 1,1-dioxide, 1-amino-4-(phenylamino)-9,10-anthraquinone-2-sulfonic acid (CI62055; Acid Blue No. 25), 2-(1,3-dihydro-3-oxo-5-sulfo-2H-indol-2-ylidene)-2,3-dihydro-3-oxo-1H-indole-5-sulfonic acid disodium salt (CI73015; Acid Blue No. 74), 9-(2-carboxyphenyl)-3-[(2-methylphenyl)amino]-6-[(2-methyl-4-sulfophenyl)amino]xanthylium internal salt, monosodium salt (CI45190; Acid Violet No. 9), 1-hydroxy-4-[(4-methyl-2-sulfophenyl)amino]-9,10-anthraquinone sodium salt (CI60730; D&C Violet No. 2; Acid Violet No. 43), bis[3-nitro-4-[(4-phenylamino)-3-sulfophenylamino]phenyl]sulfone (CI10410; Acid Brown No. 13), 5-amino-4-hydroxy-6-[(4-nitrophenyl)azo]-3-(phenylazo)-2,7-naphthalenedisulfonic acid disodium salt (CI20470; Acid Black No. 1), 3-hydroxy-4-[(2-hydroxynaphth-1-yl)azo]-7-nitro-1-naphthalenesulfonic acid-chromium complex (3:2) (CI15711; Acid Black No. 52), 3-[(2,4-dimethyl-5-sulfophenyl)azo]-4-hydroxy-1-naphthalenesulfonic acid disodium salt (CI14700; Food Red No. 1; Ponceau SX; FD&C Red No. 4), 4-(acetylamino)-5-hydroxy-6-[(7-sulfo-[(4-sulfophenyl)azo]naphth-1-yl)azo]-1,7-naphthalenedisulfonic acid tetrasodium salt (CI28440; Food Black No. 1) and 3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195).

The colorant (b) according to the invention, which is characterized by a content of an oxidizing agent, preferably hydrogen peroxide, can, besides the dyes of the general formula (I), additionally also comprise further oxidation-stable direct dyes, such as, for example, 3-(2',6'-diaminopyridyl-3'-azo)pyridine (=2,6-diamino-3-((pyridin-3-yl)azo)pyridine), N,N-di(2-hydroxyethyl)-3-methyl-4-((4-nitrophenyl)azo) aniline (Disperse Red 17, CI11210), 3-diethylamino-7-(4-dimethylaminophenylazo)-5-phenylphenazinium chloride (Cl11050), 4-(2-thiazolylazo)resorcinol, 4-((4-phenylamino) azo)benzosulfonic acid sodium salt (Orange IV), 1-((3-aminopropyl)amino)-9,10-anthracenedione (HC Red No. 8), 3',3'',4,5,5',5'',6,7-octabromophenol sulfonephthalein (tetrabromophenol Blue), 1-((4-amino-3,5-dimethylphenyl)(2,6-dichlorophenyl)methylene)-3,5-dimethyl-4-imino-2,5-cyclohexadiene-phosphoric acid (1:1) (Basic Blue 77), 3',3'',5',5''-tetrabromo-m-cresol sulfonephthalein, 2,4-dinitro-1-naphthol-7-sulfonic acid disodium salt (Acid Yellow 1, CI 10316), 4-[2'-hydroxy-1'-naphthyl)azo]benzosulfonic acid sodium salt (Acid Orange 7, C 15510), 3',6'-dihydroxy-2',4',5',7'-tetraiodospiro [isobenzofuran-1(3H), 9'-(9H)xanthen]-3-one disodium salt (Acid Red 51, C145430), 6-hydroxy-5-((2-methoxy-5-methyl-4-sulfophenyl)azo)-2-naphthalenesulfonic acid disodium salt (FD&C Red 40, CI16035), 2,4-dinitro-1-naphthol sodium salt (Acid Yellow 24; C110315), 2',4',5',7'-tetrabromo-4,5,6,7-tetrachloro-3',6'-dihydroxyspiro(isobenzofuran-1(3H), 9'-[9H]xanthen]-3-one disodium salt (Acid Red 92; C145410), 4-(2-hydroxy-1-naphthylazo)-3-methylbenzenesulfonic acid sodium salt (Acid Orange 8, Cl15575), 2-amino-1,4-naphthalenedione, dithizone (1,5-diphenylthiocarbazone), N-((2-hydroxyethyl)-2-nitro-4-trifluoromethyl)aniline (HC Yellow 13), N-(2-hydroxyethyl)-4-nitroaniline and 4-chloro-N-(2,3-dihydroxypropyl)-2-nitroaniline, 1-methyl-4-((methylphenylhydrazono)methyl)pyridinium methylsulfate (Basic Yellow No. 87), 3-((4,5-dihydro-3-methyl-5-oxo-1-phenyl-1H-pyrazol-4-yl)azo)-N,N,N-trimethylbenzenaminium chloride, 3-[(3-methyl-5-hydroxy-1-phenyl-1H-pyrazol-4-yl) azo]-trimethylammoniobenzene chloride (Basic Yellow No. 57), 2-((4-aminophenyl)azo)-1,3-dimethyl-1H-imidazol-3-ium chloride (Basic Orange No. 31), 1,4-dimethyl-5-[(4-(dimethylamino)phenyl)azo]-1,2,4-triazolium chloride (Basic Red No. 22, CI11055), 2-((4-(dimethylamino)-phenyl) azo)-1,3-dimethyl-1H-imidazolium chloride (Basic Red No. 51), 1,4-dimethyl-5-[[4-[methyl(phenylmethyl)amino]phenyl]azo]-1,2,4-triazolium bromide (Basic Red No. 46), N,N,N-trimethyl-3-{[4-(methylamino)-9, 10-dioxo-9,10-dihydro-1-anthracenyl]amino}-1-propanaminium methylsulfate, N,N-dimethyl-3-{[4-(methylamino)-9,10-dioxo-9,10-dihydro-1-anthracenyl]amino}-N-propyl-1-propanaminium chloride and N,N-dimethyl-3-{[4-(methylamino)-9,10-dioxo-9,10-dihydro-1-anthracenyl]amino}-N-propyl-1-propanaminium bromide.

The total content of additional dyes in the colorant according to the invention is about 0.01 to 15% by weight, in particular 0.1 to 12% by weight.

The oxidation colorant (c) according to the invention which is mixed prior to application with an oxidizing agent (in particular hydrogen peroxide or its addition compounds) comprises, besides the dyes of the general formula (I), additionally oxidation dye precursors and if necessary one or more of the abovementioned direct dyes provided these are stable to the oxidizing agent used.

Suitable oxidation dye precursors which may be specified are, for example, the following developer substances and coupler substances and self-coupling compounds:

(i) Developer substances: 1,4-diaminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-(2-(acetylamino)ethoxy)-1,4-diaminobenzene, 4-phenylaminoaniline, 4-dimethylaminoaniline, 4-diethylaminoaniline, 4-dipropylaminoaniline, 4-[ethyl(2-hydroxyethyl)-amino] aniline, 4-[di(2-hydroxyethyl)amino]aniline, 4-[di(2-hydroxyethyl)-amino]-2-methylaniline, 4-[(2-methoxyethyl)amino]aniline, 4-[(3-hydroxypropyl) amino]aniline, 4-[(2,3-dihydroxypropyl)amino]aniline, 1,4-diamino-2-(2-hydroxyethyl)benzene, 1,4-diamino-2-(1-methylethyl)-benzene, 1,3-bis[(4-aminophenyl)(2-hydroxyethyl)amino]-2-propanol, 1,4-bis[(4-aminophenyl) amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl) amino]methylphenol, 4-amino-2-methylphenol, 4-amino-2-(methoxymethyl)phenol, 4-amino-2-(2-hydroxyethyl) phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, alone or in a mixture with one another.

(ii) Coupler substances: N-(3-dimethylaminophenyl)urea, 2,6-diaminopyridine, 2-amino-4-[(2-hydroxyethyl) amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl) amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy)propane, di(2,4-diamino-phenoxy)methane, 1,3-diamino-2,4-dimethoxybenzene, 2,6-bis(2-hydroxyethyl) aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)-amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolenedione, alone or in a mixture with one another.

(iii) Self-coupling compounds: 2-amino-5-methylphenol, 2-amino-6-methylphenol, 2-amino-5-ethoxyphenol or 2-propylamino-5-aminopyridine.

The total amount of the oxidation dye precursors present in the colorant (c) according to the invention is about 0.01 to 12% by weight, in particular about 0.2 to 6% by weight.

To increase the color intensity, the carriers customary in cosmetic systems can be added if required. Suitable compounds are described, for example, in DE-A 196 18 595, to which reference is expressly made here. Particularly suitable carriers are, for example, benzyl alcohol, vanillin and isovanillin.

For coloring, the dyes described above are applied in a suitable color carrier mass.

The colorant (a), (b) or (c) according to the invention can also comprise all additives customary and known for such preparations, for example perfume oils, complexing agents, waxes, preservatives, thickeners, antioxidants, alginates, guar gum, haircare substances, such as, for example, cationic polymers or lanolin derivatives, or anionic, nonionic, amphoteric or cationic surface-active substances. Preference is given to using amphoteric or nonionic surface-active substances, for example betaine surfactants, propionates and glycinates, such as, for example, cocoamphoglycinates or cocoamphodiglycinates, ethoxylated surfactants with 1 to 1000 ethylene oxide units, preferably with 1 to 300 ethylene oxide units, such as, for example, glyceride alkoxylates, for example castor oil ethoxylated with 25 ethylene oxide units, polyglycolamides, ethoxylated alcohols and ethoxylated fatty alcohols (fatty alcohol alkoxylates) and ethoxylated fatty acid sugar esters, in particular ethoxylated sorbitan fatty acid esters. The above-mentioned constituents are used in the amounts customary for such purposes, for example the surface-active substances in a concentration of from 0.1 to 30% by weight, and the care substances in an amount of from 0.1 to 5% by weight.

The colorant (a), (b) or (c) according to the invention can, particularly if it is a hair colorant, be present in the form of a powder or granules which is/are dissolved prior to application in an aqueous or aqueous-alcoholic preparation, or else in the form of an aqueous or aqueous-alcoholic solution, a cream, a gel, an emulsion or an aerosol foam, where the colorant can be formulated either in the form of a single-component preparation or else in the form of a multicomponent preparation, for example in the form of a two-component preparation in which the particular dye derivative of the general formula (I) is packaged separately from the other constituents and the ready-to-use colorant is only prepared directly prior to application by mixing the two components.

The colorant (a), (b) or (c) according to the invention generally has a pH of about 2 to 11, preferably about 5 to 10. Both organic and inorganic acids or bases are suitable for adjusting the pH according to the invention. Examples of suitable acids are, in particular, the following acids:

α-hydroxycarboxylic acids, such as, for example, glycolic acid, lactic acid, tartaric acid, citric acid or malic acid, ascorbic acid, gluconic acid lactone, acetic acid, hydrochloric acid or phosphoric acid, and mixtures of these acids. Examples of suitable bases are, in particular, sodium carbonate, sodium hydrogencarbonate, organic amines, for example monoethanolamine, triethanolamine, 2-amino-2-methyl-1-propanol or tris(hydroxymethyl)aminomethane, ammonia, potassium hydroxide and sodium hydroxide, and mixtures thereof.

Depending on the intended use, the colorant according to the invention can be used with one or more oxidizing agents (lightening; oxidation colorants) or without an oxidizing agent (nonoxidative colorants).

If required, the agent is mixed prior to application with an oxidizing agent. Suitable oxidizing agents are primarily hydrogen peroxide or its addition compounds onto urea, melamine, sodium borate or sodium carbonate in the form of a 1 to 12% strength, preferably a 3 to 9% strength, aqueous solution. In the case of agents with simultaneous lightening or bleaching, depending on the dye of the formula (I) used it is additionally possible to also add persulfates, e.g. ammonium persulfate, potassium persulfate or sodium persulfate. The weight ratio between color carrier mass and oxidizing agent is here preferably about 5:1 to 1:3, in particular 1:1 to 1:2. Larger amounts of oxidizing agent are used especially at higher concentrations of oxidative dye precursors in the colorant, or if greater bleaching of the keratin fibers (in particular of the hair) is intended at the same time.

The colorant according to the invention is generally used by applying an amount of the hair colorant sufficient for the hair coloring, about 30 to 200 grams depending on hair length, to the hair, allowing the hair colorant to act at about 15 to 50 degrees Celsius for about 1 to 60 minutes, preferably 5 to 30 minutes, then rinsing the hair thoroughly with water, optionally washing with a shampoo and/or after-treating with a hair-conditioning composition and finally drying.

In addition, if no oxidizing agents are added to the coloring mass, the above-described colorant can comprise natural or synthetic polymers or modified polymers of natural origin customary for cosmetic compositions, as a result of which setting of the hair is achieved at the same time as the coloring. Such compositions are generally referred to as tinting setting compositions or color setting compositions.

Of the synthetic polymers known for this purpose in cosmetics, mention may be made, for example, of polyvinylpyrrolidone, polyvinyl acetate, polyvinyl alcohol or polyacrylic compounds, such as polyacrylic acid or polymethacrylic acid, basic polymers of esters of polyacrylic acid, polymethylacrylic acid and amino alcohols, for example salts or quaternization products thereof, polyacrylonitrile, polyvinyl acetates, and copolymers of such compounds, such as, for example, polyvinylpyrrolidone-vinyl acetate; while natural polymers or modified natural polymers which can be used are, for example, chitosan (deacetylated chitin) or chitosan derivatives.

The abovementioned polymers may be present in the colorant (a) according to the invention in the amounts customary for such agents, in particular in an amount of from about 1 to 5% by weight. The pH of the tinting setting composition or color setting composition according to the invention is preferably about 4 to 10.

The hair colorant with additional setting is used in a known and customary manner by wetting the hair with the setting composition, arranging (styling) the hair into the hairstyle and then drying.

The colorant according to the invention permits a coloration of keratin fibers, in particular of human hair, with the application together with hydrogen peroxide, and application to damaged hair (e.g. bleached or permed hair) allowing a particularly long-lasting coloration.

The dyes of the formula (I) can be prepared in a 2-step process analogously to known preparation processes, such as, for example, via azo coupling of 2-aminothiazole derivatives, 2-aminoimidazole derivatives, 2-aminothiadiazole derivatives or the like, with coupling components such as aniline derivatives, phenol derivatives or heterocyclic compounds. The resulting neutral azo dye is converted to the zwitterionic azo dye of the formula (I) using sultones, such as, for example, butane sultone or propane sultone.

The examples below are intended to illustrate the subject-matter of the invention in more detail without limiting it thereto.

EXAMPLES

Example 1

Synthesis of Thiazolium Butanesulfonates

Example 1a

Synthesis of 4-(2-{[4-(dimethylamino)phenyl]diazenyl}-1,3-thiazol-3-ium-3-yl)-1-butanesulfonate 8.5 g (36.6 mmol) of N,N-dimethyl-4-[1,3-thiazol-2-yldiazenyl]aniline are heated with 85 ml of butane sultone at 110° C. for 6 hours. After cooling, 200 ml of tetrahydrofuran are added to the reaction mixture and the precipitated product is filtered off, washed with acetone and dried. The dye is recrystallized with methanol/ethyl acetate. 11.8 g (87% of theory) of 4-(2-{[4-(dimethylamino)phenyl]diazenyl}-1,3-thiazol-3-ium-3-yl)-1-butanesulfonate are obtained as a dark blue power.

$^1$H NMR (300 MHz, CD3OD): δ=8.10 (d, J=9.3, 1H, H(2)-phenyl); 7.85 (d, J=4.5, 1H, H(4)-thiazole); 7.68 (d, J=9.3, 1H, H(6)-phenyl); 7.45 (d, J=4.5, 1H, H(5)-thiazole); 7.06 (d, J=9.3, 1H, H(5)-phenyl); 7.00 (d, J=9.3, 1H, H(3)-phenyl); 4.52 (t, J=7.5, 2H, N$^+$CH2); 2.79 (t, J=7.5, 2H, CH2-SO3$^-$); 2.05 (quintett, J=7.5, 2H, CH2); 1.75 (quintett, J=7.5, 2H, CH2).

API-ES MS: 369 [M$^+$+1] (45), 391 [M$^+$+Na] (100)

CHN analysis:

| ($C_{15}H_{20}N_4O_3S_2$*$H_2O$) | % C | % H | % N | % S |
|---|---|---|---|---|
| calculated | 46.61 | 5.74 | 14.50 | 16.59 |
| found | 46.30 | 5.70 | 14.20 | 16.60 |

Example 1b 4-(2-{[4-(dimethylamino)phenyl]diazenyl}-4-methyl-1,3-thiazol-3-ium-3-yl)-1-butanesulfonate Analogously to the process described in example 1a, 4-(2-{[4-(dimethylamino)phenyl]diazenyl}-4-methyl-1,3-thiazol-3-ium-3-yl)-1-butanesulfonate is prepared from N,N-dimethyl-4-[4-methyl-1,3-thiazol-2-yldiazenyl]aniline in 84% yield.

API-ES MS: 405 [M$^+$+Na] (100)

Example 1c 4-(2-{[4-(dimethylamino)phenyl]diazenyl}-5-methyl-1,3-thiazol-3-ium-3-yl)-1-butanesulfonate Analogously to the process described in example 1a, 4-(2-{[4-(dimethylamino)phenyl]diazenyl}-5-methyl-1,3-thiazol-3-ium-3-yl)-1-butanesulfonate is prepared from N,N-dimethyl-4-[5-methyl-1,3-thiazol-2-yldiazenyl]aniline in 85% yield.

API-ES MS: 405 [M$^+$+Na] (100)

Example 1d 4-(2-{[4-(dimethylamino)phenyl]diazenyl}-4,5-dimethyl-1,3-thiazol-3-ium-3-yl)-1-butanesulfonate Analogously to the process described in example 1a, 4-(2-{[4-(dimethylamino)phenyl]diazenyl}-4,5-dimethyl-1,3-thiazol-3-ium-3-yl)-1-butanesulfonate is prepared from N,N-dimethyl-4-[4,5-dimethyl-1,3-thiazol-2-yldiazenyl]aniline in 46% yield.

API-ES MS: 419 [M$^+$+Na] (100)

Example 1e

4-[2-({4-[benzyl(ethyl)amino]phenyl}diazenyl)-13-thiazol-3-ium-3-yl]-1-butanesulfonate Analogously to the process described in example 1a, 4-[2-({4-[benzyl(ethyl)amino]phenyl}diazenyl)-1,3-thiazol-3-ium-3-yl]-1-butanesulfonate is prepared from N-benzyl-N-ethyl-4-[(1,3-thiazol-2-yldiazenyl]aniline in 90% yield.

API-ES MS: 467 [M$^+$+Na] (100)

Example 2

Synthesis of 3-(2-{[4-(dimethylamino)phenyl]diazenyl}-1,3-thiazol-3-ium-3-yl)-1-propanesulfonate 0.5 g (1.5 mmol) of N,N-dimethyl-4-[1,3-thiazol-2-yldiazenyl]aniline are dissolved in 1-methyl-2-pyrrolidinone (NMP), and 0.9 g (7.5 mmol) of 1,3-propane sultone is added. The reaction mixture is heated at, 100° C. for 4 hours. After cooling, 20 ml of tetrahydrofuran are added to the reaction mixture and the precipitated product is filtered off, washed with acetone and dried. The resulting dye is recrystallized from methanol/ethyl acetate. 0.53 g (45% of theory) of 3-(2-{[4-(dimethylamino)phenyl]diazenyl}-1,3-thiazol-3-ium-3-yl)-1-propanesulfonate is obtained as a dark blue powder.

$^1$H NMR (300 MHz, CD3OD): δ=8.20 (d, J=9.0, 1H, H(2)-phenyl); 7.88 (d, J=4.5, 1H, H(4)-thiazole); 7.71 (d, J=9.0, 1H, H(6)-phenyl); 7.45 (d, J=4.5, 1H, H(5)-thiazole); 7.08 (d, J=9.0, 1H, H(5)-phenyl); 7.03 (d, J=9.0, 1H, H(3)-phenyl); 4.7 (t, J=7.2, 2H, N$^+$CH2); 3.35 (s, 6H, N—CH3); 2.82 (t, J=7.2, 2H, CH2-SO3$^-$); 2.34 (quintett, J=7.2, 2H, CH2).

API-ES MS: 377 [M$^+$+Na] (100)

Coloring Examples 3 to 8

Hair Colorant

| | |
|---|---|
| 2.5 mmol | Dye of the formula (I) |
| 5.0 g | Ethanol |
| 4.0 g | Decyl glucoside |
| 0.2 g | Ethylenediaminotetraacetic acid disodium salt |
| ad 100.0 g | Water, demineralized |

If necessary, the coloring solution is adjusted to the pH values given in table 1 by adding ammonia.

The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed with lukewarm water and then dried.

The coloring results are summarized in table 1 below.

TABLE 1

| Ex. | Compound of the formula (I) (as in examples 1a to 1e and 2) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 3 | 4-(2-{[4-(dimethylamino)phenyl]diazenyl}-1,3-thiazol-3-ium-3-yl)-1-butanesulfonate (1a) | 6.4 | blue | L = 17.41<br>C = 27.76<br>h = 314.30 |
| 4 | 4-(2-{[4-(dimethylamino)phenyl]diazenyl}-4-methyl-1,3-thiazol-3-ium-3-yl)-1-butanesulfonate (1b) | 6.2 | blue | L = 30.54<br>C = 40.12<br>h = 295.30 |
| 5 | 4-(2-{[4-(dimethylamino)phenyl]diazenyl}-5-methyl-1,3-thiazol-3-ium-3-yl)-1-butanesulfonate (1c) | 6.5 | blue | L = 18.56<br>C = 39.85<br>h = 307.40 |
| 6 | 4-(2-{[4-(dimethylamino)phenyl]diazenyl}-4,5-dimethyl-1,3-thiazol-3-ium-3-yl)-1-butanesulfonate (1d) | 6.4 | blue | L = 20.65<br>C = 37.53<br>h = 298.60 |
| 7 | 4-[2-({4-[benzyl(ethyl)amino]-phenyl}diazenyl)-1,3-thiazol-3-ium-3-yl]-1-butanesulfonate (1e) | 7.2 | blue | L = 27.15<br>C = 49.93<br>h = 305.10 |
| 8 | 3-(2-{[4-(dimethylamino)-phenyl]diazenyl}-1,3-thiazol-3-ium-3-yl)-1-propane-sulfonate (2) | 6.6 | blue | L = 18.62<br>C = 35.81<br>h = 312.00 |

Coloring Example 9

Hair Colorant with Cationic Surface-Active Substances

| | |
|---|---|
| 0.91 g | 4-(2-{[4-(dimethylamino)phenyl]diazenyl}-1,3-thiazol-3-ium-3-yl)-1-butanesulfonate (1a) |
| 5.00 g | Ethanol |
| 4.00 g | Cetyltrimethylammonium chloride, 25% in water |
| ad 100.00 g | Water, demineralized |

The pH is adjusted to 9.2 using 25% strength ammonia.

The hair coloring is carried out by applying an amount of the colorant sufficient for the hair coloring to the hair and distributing it evenly using a brush. After a contact time of 30 minutes at 40° C., the hair (L=80.6; C=12.1; h=92.1) is rinsed with lukewarm water, washed with a shampoo, rinsed again with lukewarm water and then dried.

This gives an intensely blue colored tress (L=20.85; C=43.76; h=312.10).

Coloring Example 10

Hair Colorant with Amphoteric Surface-Active Substances

| | |
|---|---|
| 0.91 g | 4-(2-{[4-(dimethylamino)phenyl]diazenyl}-1,3-thiazol-3-ium-3-yl)-1-butanesulfonate (1a) |
| 5.00 g | Ethanol |
| 7.50 g | Coconut fatty acid amidopropylbetaine |
| ad 100.00 g | Water, demineralized |

The pH is adjusted to 9.2 using 25% strength ammonia.

The hair coloring is carried out by applying an amount of the colorant sufficient for the hair coloring to the hair and distributing it evenly using a brush. After a contact time of 30 minutes at 40° C., the hair (L=80.6; C=12.1; h=92.1) is rinsed with lukewarm water, washed with a shampoo, rinsed again with lukewarm water and then dried.

This gives an intensely blue colored tress (L=18.36; C=31.57; h=314.90).

Coloring Example 11

Hair Colorant with Anionic Surface-Active Substances

| | |
|---|---|
| 0.91 g | 4-(2-{[4-(dimethylamino)phenyl]diazenyl}-1,3-thiazol-3-ium-3-yl)-1-butanesulfonate (1a) |
| 5.00 g | Ethanol |
| 7.50 g | Lauryl ether sulfate, 28% in water |
| ad 100.00 g | Water, demineralized |

The pH is adjusted to 9 using 25% strength ammonia.

The hair coloring is carried out by applying an amount of the colorant sufficient for the hair coloring to the hair and distributing it evenly using a brush. After a contact time of 30 minutes at 40° C., the hair (L=80.6; C=12.1; h=92.1) is rinsed with lukewarm water, washed with a shampoo, rinsed again with lukewarm water and then dried.

This gives an intensely blue colored tress (L=20.70; C=43.67; h=312.30).

Coloring Examples 12-17

Hair Colorant with Oxidizing Agent

| | |
|---|---|
| 0.6 g | Dye of the formula (I) as in table 2 |
| 5.0 g | Ethanol |
| 4.0 g | Decyl glucoside |
| 0.2 g | Ethylenediaminotetraacetic acid disodium salt |
| ad 100.0 g | Water, demineralized |

5 g of the above color carrier mass are mixed with 5 g of a 9% strength hydrogen peroxide solution. The pH is adjusted to 9.5 using 25% strength ammonia.

The resulting ready-to-use hair colorant is applied to the hair and distributed evenly using a brush. After a contact time of 30 minutes at 40° C., the hair is rinsed with lukewarm water, washed with a shampoo, rinsed again with lukewarm water and then dried.

The coloring results are summarized in table 2 below.

TABLE 2

| Ex. | Compound of the formula (I) (as in examples 1a to 1e and 2) | Color shade after coloring | Color measurement values after coloring |
|---|---|---|---|
| — | Color shade of the hair before the coloring treatment | — | L = 80.60<br>C = 12.10<br>h = 92.10 |
| 12 | 4-(2-{[4-(dimethylamino)phenyl]diazenyl}-1,3-thiazol-3-ium-3-yl)-1-butanesulfonate (1a) | blue | L = 18.28<br>C = 35.59<br>h = 313.30 |
| 13 | 4-(2-{[4-(dimethylamino)-phenyl]diazenyl}-4-methyl-1,3-thiazol-3-ium-3-yl)-1-butanesulfonate (1b) | blue | L = 28.33<br>C = 44.37<br>h = 298.50 |
| 14 | 4-(2-{[4-(dimethylamino)-phenyl]diazenyl}-5-methyl-1,3-thiazol-3-ium-3-yl)-1-butanesulfonate (1c) | blue | L = 19.85<br>C = 41.60<br>h = 306.40 |
| 15 | 4-(2-{[4-(dimethylamino)-phenyl]diazenyl}-4,5-dimethyl-1,3-thiazol-3-ium-3-yl)-1-butanesulfonate (1d) | blue | L = 26.69<br>C = 43.57<br>h = 293.40 |
| 16 | 4-[2-({4-[benzyl(ethyl)amino]-phenyl}diazenyl)-1,3-thiazol-3-ium-3-yl]-1-butanesulfonate (1e) | blue | L = 29.59<br>C = 51.02<br>h = 304.20 |
| 17 | 3-(2-{[4-(dimethylamino)-phenyl]diazenyl}-1,3-thiazol-3-ium-3-yl)-1-propane-sulfonate (2) | blue | L = 20.05<br>C = 44.27<br>h = 311.50 |

Coloring Examples 18 and 19

Hair Colorant with Oxidizing Agent

| | |
|---|---|
| 1.9 g | 4-(2-{[4-(dimethylamino)phenyl]diazenyl}-5-methyl-1,3-thiazol-3-ium-3-yl)-1-butanesulfonate (1c) |
| 5.0 g | Ethanol |
| 4.0 g | Decyl glucoside |
| 0.2 g | Ethylenediaminotetraacetic acid disodium salt |
| ad 100.0 g | Water, demineralized |

5 g of the above color carrier mass are mixed with 5 g of a 9% strength hydrogen peroxide solution. The pH is adjusted to 9.0 using 25% strength ammonia.

The resulting ready-to-use hair colorant is applied to natural hair (Ex. 18) and bleached natural hair (Ex. 19) and distributed evenly using a brush. After a contact time of 30 minutes at 40° C., the hair is rinsed with lukewarm water, washed with a shampoo, rinsed again with lukewarm water and then dried. The washing process is repeated five times. The colors do not change visually.

| Ex. | Hair type | Color after coloring | Color after washing |
|---|---|---|---|
| 18 | Natural hair | Dark blue | Dark blue |
| 19 | Bleached natural hair | Royal blue | Royal blue |

The L*C*h* color measurement values given in the present examples were ascertained using a colorimeter from Minolta, model Chromameter II. Here, the L value is the lightness (i.e. the lower the L value, the greater the color intensity), while the C value is a measure of the colorfulness ("chroma") (i.e. the greater the C value, the more colorful the color). The h value is the color shade angle ("hue").

Unless stated otherwise, all of the percentages given in the present application are percentages by weight.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the nonoxidative coloring of keratin fibers, comprising at least one zwitterionic azo dye of the general formula (I);

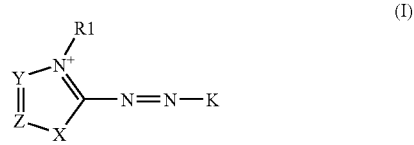

wherein
R1 is an alkyl sulfonate radical of the formula (II);

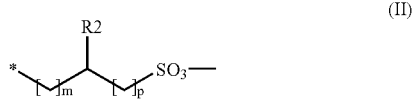

R2 is hydrogen or a hydroxyl group;

m is 0 to (n−1);

p is 0 to (n−1) where m+p=(n−1);

n is an integer from 1 to 6;

X is oxygen, sulfur, N—R3 or C—R4;

Y is C—R5, nitrogen, N—R6, sulfur or oxygen;

Z is C—R7 or nitrogen; and wherein the heterocycle of the formula (I) comprises at least two and at most three heteroatoms, where the heterocycle has at most one sulfur atom or oxygen atom; R3 and R6 may be identical or different and, independently of one another, are a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group or a substituted or unsubstituted benzyl group;

R4, R5 and R7 may be identical or different and, independently of one another, are hydrogen, a halogen atom, a saturated or unsaturated ($C_1$-$C_{12}$)-alkyl group, a ($C_1$-$C_{12}$)-alkyl group substituted by a halogen atom (F, Cl, Br, I), a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group or a naphthyl group, or a substituted or unsubstituted heteroaryl group; or if Y and Z are C—R5 and C—R7, the radical groups R5 and R7, together with the remaining molecule, can form a heterocyclic or carbocyclic, saturated or unsaturated, substituted or unsubstituted ring system;

or if X and Y are C—R4 and C—R5, the radical groups R4 and R5, together with the remaining molecule, can form a heterocyclic or carbocyclic, saturated or unsaturated, substituted or unsubstituted ring system;

K is a radical group of the aniline or phenol series or a monocyclic or polycyclic heterocyclic radical group.

2. An agent for the simultaneous lightening and coloring of keratin fibers, comprising at least one oxidizing agent, and at least one oxidizing-agent-stable zwitterionic azo dye of the general formula (I) according to claim 1.

3. An oxidative colorant for coloring fibers based on at least one oxidation dye precursor, comprising at least one oxidizing-agent-stable zwitterionic azo dye of the general formula (I) according to claim 1.

4. An agent according to claim 1, comprising at least one natural polymer customary for cosmetic agents, synthetic polymer or modified polymer of natural origin, and being in the form of a tinting setting composition or color setting composition.

5. An agent according to claim 2, wherein said oxidizing agent is selected from the group consisting of hydrogen peroxide or its addition compounds onto urea, melamine, sodium borate and sodium carbonate.

6. An agent according to claim 3, wherein said oxidizing agent is chosen from hydrogen peroxide or its addition compounds onto urea, melamine, sodium borate, sodium carbonate, and persulfates.

7. An agent according to claim 1, wherein, in said formula (I), R2 is hydrogen and n is 2 or 3.

8. An agent according to claim 7, wherein, in said formula (I), K is a radical group of the formula K1,

K1 in which R8 and R9 may be identical or different and, independently of one another, are a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group or a benzyl group, or R8 and R9, together with the nitrogen atom, form a 5-membered to 6-membered ring system, which may comprise a further heteroatom; or R8 and/or R9 form with a carbon atom of the benzene ring an optionally oxygen-containing or nitrogen containing five or six-membered heterocycle which may be substituted with one or several ($C_1$-$C_{12}$)-alkyl groups;

R10 and R11 may be identical or different and, independently of one another, are hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group.

9. An agent according to claim 1, wherein the zwitterionic azo dye of said formula (I) is selected from the group consisting of 4-(2-{[4-(dimethylamino)phenyl]diazenyl)}-1,3-thiazol-3-ium-3-yl)-1-butanesulfonate, 3-(2-{[4-(dimethylamino)phenyl]diazenyl}-1,3-thiazol-3-ium-3-yl)-1-propanesulfonate, 4-(2-{[4-(dimethylamino)phenyl]diazenyl)}-4-methyl-1,3-thiazol-3-ium-3-yl)-1-butanesulfonate, 3-(2-{[4-(dimethyl-amino)phenyl]diazenyl}-4-methyl-1,3-thiazol-3-ium-3-yl)-1-propane-sulfonate, 4-(2-{[4-(dimethylamino)phenyl]diazenyl}-5-methyl-1,3-thiazol-3-ium-3-yl)-1-butanesulfonate, 3-(2-{[4-(dimethylamino)phenyl]diazenyl}-5-methyl-1,3-thiazol-3-ium-3-yl)-1-propanesulfonate, 4-(2-{[4-(dimethyl-amino)phenyl]diazenyl}-4,5-dimethyl-1,3-thiazol-3-ium-3-yl)-1-butane-sulfonate, 3-(2-{[4-(dimethylamino)phenyl]diazenyl}-4,5-dimethyl-1,3-thiazol-3-ium-3-yl)-1-propanesulfonate, 4-(5-bromo-2-{[4-(dimethylamino)-phenyl]-diazenyl}-1,3-thiazol-3-ium-3-yl)-1-butanesulfonate, 3-(5-bromo-2-{[4-(dimethylamino)phenyl]diazenyl}-1,3-thiazol-3-ium-3-yl)-1-propane-sulfonate, 4-(2-{[4-(dimethylamino)phenyl]diazenyl}-5-methoxy-1,3-thiazol-3-ium-3-yl)-1-butanesulfonate, 3-(2-{[4-(dimethylamino)phenyl]-diazenyl}-5-methoxy-1,3-thiazol-3-ium-3-yl)-1-propanesulfonate, 4-(2-{[4-(dimethylamino)phenyl]diazenyl}-5-nitro-1,3-thiazol-3-ium-3-yl)-1-butanesulfonate, 3-(2-{[4-(dimethylamino)phenyl]diazenyl}-5-nitro-1,3-thiazol-3-ium-3-yl)-1-propanesulfonate, 4-[(2-{4-[benzyl(methyl)amino]-phenyl}diazenyl)-1,3-thiazol-3-ium-3-yl]-1-butanesulfonate, 3-[(2-{4-[benzyl(methyl)amino]phenyl}diazenyl)-1,3-thiazol-3-ium-3-yl]-1-propanesulfonate, 4-(2-{[4-(1-pyrrolidinyl)phenyl]diazenyl}-1,3-thiazol-3-ium-3-yl)-1-butanesulfonate, 3-(2-{[4-(1-pyrrolidinyl)phenyl]diazenyl}-1,3-thiazol-3-ium-3-yl)-1-propanesulfonate, 4-(2-{[4-(4-morpholinyl)phenyl]- diazenyl}-1,3-thiazol-3-ium-3-yl)-1-butanesulfonate, 3-(2-{4-(4-morpholinyl)phenyl]diazenyl}-1,3-thiazol-3-ium-3-yl)-1-propanesulfonate, 4-(2-{[4-(4-methyl-1-piperazinyl)phenyl]diazenyl}-1,3-thiazol-3-ium-3-yl)-1-butanesulfonate, 3-(2-{[4-(4-methyl-1-piperazinyl)-phenyl]diazenyl}-1,3-thiazol-3-ium-3-yl)-1-propanesulfonate, 4-[2-(2,3,6,7-tetrahydro-1H,5H-pyrido [3,2,1-ij]quinolin-9-yldiazenyl)-1,3-thiazol-3-ium-3-yl]-1-butanesulfonate, 4-[2-(2,3,6,7-tetrahydro-1H,5H-pyrido[3,2,1-ij]quinolin-9-yldiazenyl)-1,3-thiazol-3-ium-3-yl]-1-propanesulfonate, 4-[5-methyl-2-(2,3,6,7-tetrahydro-1H,5H-pyrido [3,2,1-ij]quinolin-9-yldiazenyl)-1,3-thiazol-3-ium-3-yl]-1-butane-sulfonate, 4-[5-methyl-2-(2,3,6,7-tetrahydro-1H,5H-pyrido [3,2,1-ij]quinolin-9-yldiazenyl)-1,3-thiazol-3-ium-3-yl]-1-propanesulfonate, 4-[4-methyl-2-(2,3,6,7-tetrahydro-1H,5H-pyrido[3,2,1-ij]quinolin-9-yldiazenyl)-1,3-thiazol-3-ium-3-yl]-1-butanesulfonate, 4-[4-methyl-2-(2,3,6,7-tetrahydro-1H,5H-pyrido[3,2,1-ij]quinolin-9-yldiazenyl)-1,3-thiazol-3-ium-3-yl]-1-propanesulfonate, 4-[4,5-dimethyl-2-(2,3,6,7-tetrahydro-1H,5H-pyrido[3,2,1-ij]quinolin-9-yldiazenyl)-1,3-thiazol-3-ium-3-yl]-1-butanesulfonate, 4-[4,5-dimethyl-2-(2,3,6,7-tetrahydro-1H,5H-pyrido[3,2,1-ij]quinolin-9-yldiazenyl)-1,3-thiazol-3-ium-3-yl]-1-propanesulfonate, 2-{[4-(dimethylamino)phenyl]diazenyl}-1,3-benzothiazol-3-ium-3-yl)-1-butanesulfonate, 3-(2-{[4-(dimethylamino)phenyl]diazenyl}-1,3-benzothiazol-3-ium-3-yl)-1-propanesulfonate, 4-(2-{[4-(dimethylamino)-phenyl]diazenyl }-6-methoxy-1,3-benzothiazol-3-ium-3-yl)-1-butane-sulfonate, 3-(2-{[4-(dimethylamino)phenyl]diazenyl}-6-methoxy-1,3-benzothiazol-3-ium-3-yl)-1-propanesulfonate, 4-[2-({4-[benzyl(ethyl)-amino]phenyl}diazenyl)-1,3-thiazol-3-ium-3-yl]-1-butanesulfonate, 3-[2-({4-[benzyl(ethyl)amino]-phenyl}diazenyl)-1,3-thiazol-3-ium-3-yl]-1-propanesulfonate, 4-[2-({4-[benzyl(ethyl)amino]phenyl}diazenyl)-4-methyl-1,3-thiazol-3-ium-3-yl]-1-butanesulfonate, 3-[2-({4-[benzyl(ethyl)amino]phenyl}diazenyl)-4-methyl-1,3-thiazol-3-ium-3-yl]-1-propanesulfonate, 4-[2-({4-[benzyl(ethyl)amino]phenyl}diazenyl)-5-methyl-1,3-thiazol-3-ium-3-yl]-1-butanesulfonate, 3-[2-({4-[benzyl(ethyl)amino]phenyl}diazenyl)-5-methyl-1,3-thiazol-3-ium-3-yl]-1-propanesulfonate, 4-[2-({4-[benzyl(ethyl)-amino]phenyl}diazenyl)-4,5-dimethyl-1,3-thiazol-3-ium-3-yl]-1-butanesulfonate, 3-[2-({4-[benzyl(ethyl)amino]phenyl}diazenyl)-4,5-dimethyl-1,3-thiazol-3-ium-3-yl]-1-propanesulfonate, 4-[2-({4-[benzyl-(ethyl)amino]-2-methylphenyl }diazenyl)-1,3-thiazol-3-ium-3-yl]-1-butanesulfonate, 3-[2-({4-[benzyl(ethyl)amino]-2-methylphenyl}diazenyl)-1,3-thiazol-3-ium-3-yl]-1-propanesulfonate, 4-[2-({4-[benzyl(ethyl)amino]-2-methylphenyl}diazenyl)-4-methyl-1,3-thiazol-3-ium-3-yl]-1-butane-sulfonate, 3-[2-({4-[benzyl(ethyl)amino]-2-methylphenyl}diazenyl)-4-methyl-1,3-thiazol-3-ium-3-yl]-1-propanesulfonate, 4-[2-({4-[benzyl(ethyl)-amino]-2-methylphenyl}diazenyl)-5-methyl-1,3-thiazol-3-ium-3-yl]-1-butanesulfonate, 3-[2-({4-[benzyl(ethyl)amino]-2-methylphenyl}diazenyl)-5-methyl-1,3-thiazol-3-ium-3-yl]-1-propanesulfonate, 4-[2-({4-[benzyl-(ethyl)amino]-2-methylphenyl}diazenyl)-4,5-dimethyl-1,3-thiazol-3-ium-3-yl]-1-butanesulfonate, 3-[2-({4-[benzyl(ethyl)amino]-2-methylphenyl}-diazenyl)-4,5-dimethyl-1,3-thiazol-3-ium-3-yl]-1-propanesulfonate, 4-(2-{[4-(dimethylamino)phenyl]diazenyl}-1-methyl-1H-imidazol-3-ium-3-yl)-1-butanesulfonate, 3-(2-{[4-(dimethylamino)phenyl]diazenyl}-1-methyl-1H-imidazol-3-ium-3-yl)-1-propanesulfonate, 4-{2-[(4-aminophenyl)-diazenyl]-1-methyl-1H-imidazol-3-ium-3-yl}-1-butanesulfonate, 3-{2-[(4-aminophenyl)diazenyl]-1-methyl-1H-imidazol-3-ium-3-yl}-1-propanesulfonate, 4-(1-methyl-2-{[4-(methylamino)phenyl]diazenyl}-1H-imidazol-3-ium-3-yl)-1-butanesulfonate, 3-(1-methyl-2-{[4-(methylamino)-phenyl]diazenyl}-1H-imidazol-3-ium-3-yl)-1-propanesulfonate, 4-(2-{[4-(dimethylamino)phenyl]diazenyl}-1,4,5-trimethyl-1H-imidazol-3-ium-3-yl)-1-butanesulfonate, 3-(2-{[4-(dimethylamino)phenyl]diazenyl}-1,4,5-trimethyl-1H-imidazol-3-ium-3-yl)-1-propanesulfonate, 4-(5-{[4-(dimethylamino)phenyl]diazenyl}-4-methyl-4H-1,2,4-triazol-1-ium-1-yl)-1-butanesulfonate, 3-(5-{[4-(dimethylamino)phenyl]diazenyl}-4-methyl-4H-1,2,4-triazol-1-ium-1-yl)-1-propanesulfonate, 4-(2-{[4-(dimethylamino)phenyl]diazenyl}-1,3,4-thiadiazol-3-ium-3-yl)-1-butanesulfonate, 3-(2-{[4-(dimethylamino)phenyl]diazenyl}-1,3,4-thiadiazol-3-ium-3-yl)-1-propanesulfonate, 4-(5-{[4-(dimethylamino)-phenyl]diazenyl}-1,2,4-thiadiazol-4-ium-4-yl)-1-butanesulfonate, 3-(5-{[4-(dimethylamino)phenyl]diazenyl}-1,2,4-thiadiazol-4-ium-4-yl)-1-propanesulfonate, 3-(3-{[4-(dimethylamino)phenyl]diazenyl}-1-methyl-1H-pyrazol-2-ium-2-yl)-1-propanesulfonate, 4-(3-{[4-(dimethylamino)phenyl]-diazenyl}-1-methyl-1H-pyrazol-2-ium-2-yl)-1-butanesulfonate, 3-(3-{[4-(dimethylamino)phenyl]diazenyl}isoxazol-2-ium-2-yl)-1-propanesulfonate, 4-(3-{[4-(dimethylamino)phenyl]diazenyl}isoxazol-2-ium-2-yl)-1-butanesulfonate, 4-{2-[(1-methyl-2-phenyl-1H-indol-3-yl)diazenyl]-1,3-thiazol-3-ium-3-yl}-1-butanesulfonate, 3-{2-[(1-methyl-2-phenyl-1H-indol-3-yl)diazenyl]-1,3-thiazol-3-ium-3-yl}-1-propanesulfonate, 4-{2-(1,2-dimethyl-1H-indol-3-yl)diazenyl]-1,3-thiazol-3-ium-3-yl}-1-butane-sulfonate and 3-{2-(1,2-dimethyl-1H-indol-3-yl)diazenyl]-1,3-thiazol-3-ium-3-yl}-1-propanesulfonate.

10. An agent according to claim 1, wherein the zwitterionic azo dye of said formula (I) is present in an amount of from 0.01 to 10% by weight.

11. An agent according to claim 1, wherein the agent additionally comprises at least one further direct dye selected from the group consisting of nitro dyes, azo dyes, anthraquinone dyes, triphenylmethane dyes and basic or acidic dyes.

12. An agent according to claim 11, wherein said additional direct dye is present in a total amount of from 0.01 to 15% by weight.

13. An agent according to claim 1, wherein the agent has a pH of from 2 to 11.

14. An agent according to claim 1, wherein the agent is a hair colorant.

* * * * *